(12) United States Patent
Wang et al.

(10) Patent No.: US 6,372,261 B1
(45) Date of Patent: Apr. 16, 2002

(54) PROCESS FOR PRODUCING GUILU ERXIANGAO

(75) Inventors: Shu-Ching Wang; Shih-Yu Lee, both of Yung-Ho; Jenn-Ru Shaw, Chung-Li; Wei-Min Lee, Taipei, all of (TW)

(73) Assignee: Pharmaceutical Industry Technology and Development Center, Taipei, Hsien (TW)

( * ) Notice: Subject to any disclaimer, the term of this patent is extended or adjusted under 35 U.S.C. 154(b) by 0 days.

(21) Appl. No.: 09/612,831

(22) Filed: Jul. 7, 2000

(51) Int. Cl.[7] .................. A61K 35/00; A61K 35/12; A61K 35/32; A61K 35/78
(52) U.S. Cl. .................. 424/520; 424/538; 424/548; 424/725; 424/728
(58) Field of Search .................. 424/439, 400, 424/484, 520, 538, 548, 725, 728

(56) References Cited

U.S. PATENT DOCUMENTS 5,064,675 A * 11/1991 Jensen et al. ............... 426/597
5,776,460 A * 7/1998 Kim et al. ................. 424/195.1
5,866,160 A * 2/1999 Hong et al. ................ 424/451
6,093,403 A * 7/2000 Huo et al. ................. 424/195.1

OTHER PUBLICATIONS

Chen Ke–ji, M.D., Hunan Science & Technology Press—First Edition 1997, p. 260.*

* cited by examiner

Primary Examiner—Gollamudi S. Kishore
Assistant Examiner—Humera N. Sheikh
(74) Attorney, Agent, or Firm—Fish & Richardson P.C.

(57) ABSTRACT

The invention discloses a process for producing Guilu Erxian Gao used as a tonic medicine, comprising the steps of: (a) extracting medicinal materials comprising tortoise plastron and buckhorn with an edible acid to obtain an extract; (b) dialyzing the extract; (c) decocting ginseng and medlar and filtrating to obtain a filtrate; and (d) concentrating the mixtures of dialyzed extract and the filtrate to form a gel-like solid.

15 Claims, 4 Drawing Sheets

PROCESS FOR PRODUCING GUILU ERXIANGAO

BACKGROUND OF THE INVENTION

1. Field of the Invention

The present invention relates to a process for producing Guilu Erxian Gao, a traditional Chinese medicine. More particularly, it relates to a new manufacturing procedure in which the medicinal materials of tortoise plastron and buckhorn are extracted with acid, followed by mixing the filtrates of ginseng and medlar and concentrating to obtain bioactive Guilu Erxian Gao.

2. Description of the Related Arts

Guilu Erxian Gao is a traditional Chinese medicine which has been used as a form of tonic medicine in China for a long period of time. Typically, Guilu Erxian Gao is prepared from the medicinal materials such as tortoise plastron, buckhorn, ginseng and medlar, and is used as an energy supplement and tonic.

The traditional method for producing Guilu Erxian Gao can be found in ancient books. First, 2.5 kg of tortoise plastron and 5 kg of buckhorn are broken into pieces and decocted in water for 3 days with continuous heat. During the decocting period, boiling water is added frequently. Then the decoction is filtered to obtain a filtrate. Next, 940 g of medlar and 470 g of ginseng are decocted in water for 1 day, and the decoction is filtered to obtain a filtrate. The filtrates of four medicinal materials described above are pooled together and stewed to form a paste. Finally, the paste is air dried in the shade to obtain the product.

The current commercial method for producing Guilu Erxian Gao uses 100 kg of tortoise plastron, 50 kg of buckhorn, 6 kg of ginseng and 10 kg of medlar as medicinal materials. First, the tortoise plastron and buckhorn are washed and decocted in water for 4–6 days with continuous heat. During the decocting period, boiling water is added several times until the tortoise plastron and buckhorn become brittle. Then the decoction is filtered to obtain a filtrate. Next, the medlar and ginseng are decocted in water for 1 day, and the decoction is filtered to obtain a filtrate. The resulting filtrates are pooled together and stewed to form a paste. Finally, the paste is air dried in the shade to obtain the product. Alternatively, in Taiwan, during the paste stewing, the foam produced after the first boiling is removed. Alum, crystal sugar and soybean oil may be added. Sometimes wine is added.

However, there are some drawbacks in the methods described above. The time required for the manufacturing process is very long, and the steps are minute and complicated. The tortoise plastron and buckhorn are decocted at least for 3 days, and then air-dried for a long period of time to produce the final product. In addition, boiling water has to be added during the decocting process. A single careless step can cause the loss of the entire batch.

SUMMARY OF THE INVENTION

It is therefore a primary object of the present invention to provide a process for producing Guilu Erxian Gao, comprising the steps of: (a) extracting medicinal materials comprising tortoise plastron and buckhorn with an edible acid to obtain an extract; (b) dialyzing the extract; (c) decocting ginseng and medlar and filtrating to obtain a filtrate; and (d) concentrating the mixtures of dialyzed extract and the filtrate to form a gel-like solid.

Another object of the present invention is to provide a method for extracting the active protein ingredient contained in tortoise plastron and buckhorn with an acid.

BRIEF DESCRIPTION OF THE DRAWINGS

The present invention will be more fully understood and further advantages will become apparent when reference is made to the following description of the invention and the accompanying drawings in which.

DETAILED DESCRIPTION OF THE INVENTION

In accordance with the present invention, there is provided a process for producing Guilu Erxian Gao, comprising the steps of: (a) extracting medicinal materials comprising tortoise plastron and buckhorn with an edible acid to obtain an extract; (b) dialyzing the extract; (c) decocting ginseng and medlar and filtrating to obtain a filtrate; and (d) concentrating the mixtures of dialyzed extract and the filtrate to form a gel-like solid.

The advantage of the present invention is that the proteins of tortoise plastron and buckhorn are extracted with acid. The extract is then dialyzed to remove excess acid and small particles. The time required for this acid extraction process is much less than that for the traditional decoction process, and does not require the adding of boiling water. Then the resulting solution is mixed with the decoctions of ginseng and medlar, and is followed by concentration to obtain the Guilu Erxian Gao of the present invention.

The tortoise plastron according to the present invention is selected from TESTUDINIDAE, including species of *Chinemys reevesii* (Gray), *Mauremys mutica*, *Cuora amboinensis*, or *Cuora flavoarginata*.

The buckhorn used for the medicinal material is selected from the ossified horn of CERVIDAE, including species of *Cervus nippon* Temminck, *C. elaphus*, *C. albirostris* Prewalski, *C. unicolor* Kerr, *C. elaphus canadensis* or *C. macneilli* Lydekker.

Other medicinal materials used in the process of the present invention are ginseng and medlar, in which ginseng is *Panax ginseng* and medlar is the fruit of *Lycium chinensis* Mill.

Edible acids that can be used for the extraction of the proteins of tortoise plastron and buckhorn include, but are not limited to, acetic acid, phosphoric acid, tartaric acid, citric acid and the mixtures thereof, preferably phosphoric E. acid. More preferably, the pH of the acid ranges from 3.5 to 5.5.

Figure 1:
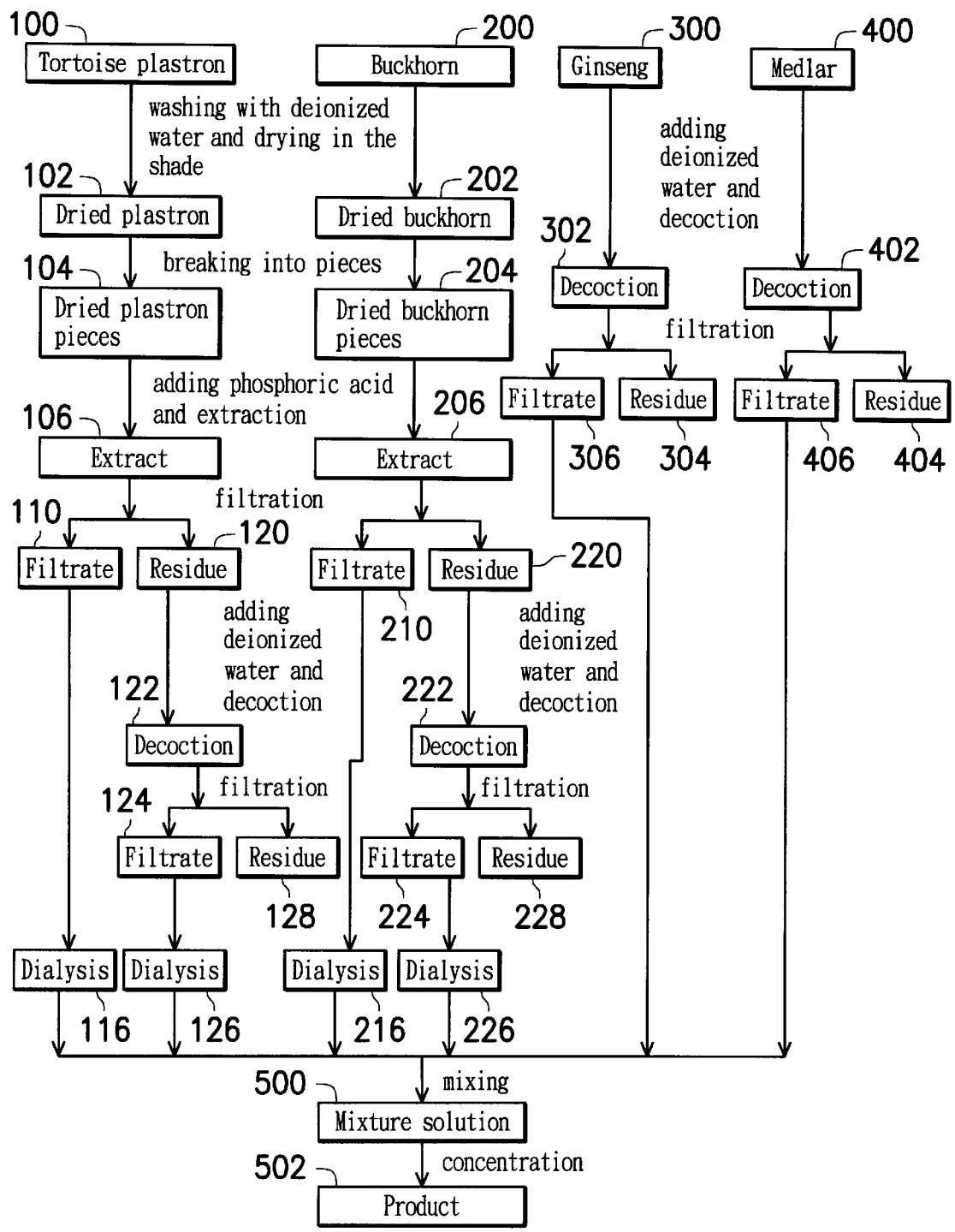
FIG. 1 is a flow chart showing the procedure of producing the Guilu Erxian Gao according to the present invention.

The flow chart of the process according to the present invention is shown in FIG. 1. The tortoise plastron and buckhorn is washed with deionized water, respectively, air dried in the shade at room temperature, and then broken into pieces. The fragments of tortoise plastron and buckhorn are extracted with an edible acid with shaking at 25~100 rpm at room temperature, respectively, which is followed by filtration to obtain a filtrate and residue. The filtrate is then dialyzed to remove excess acid and small particles. Deionized water is then added into the residue. The extraction is performed in water bath at 40~60° C. with shaking at 25~100 rpm, which is followed by filtration to obtain a filtrate. In addition, the filtrate is then dialyzed to remove acid and small particles.

In addition, deionized water is added to ginseng and medlar for decoction, respectively. The decoction is then filtrated to obtain a filtrate. The filtrates of ginseng and medlar are mixed with the dialyzed extracts of tortoise plastron and buckhorn described above. The mixture is then concentrated into the final product. The Guilu Erxian Gao produced according to the present invention has a little flavor. It is a gel-like solid with yellow-brown color and has excellent water solubility.

The dialysis step is performed through a dialysis membrane. Preferably, the membrane has a molecular weight cut off (MWCO) 3,500 Da. Thus, the molecules with molecular weight higher than 3,500 Da in the dialysis membrane are collected. Further, the concentration step according to the present invention is a well-known technique in this art. The concentration step can be performed in any conventional manner, for example, in vacuum under reduced pressure.

The active protein ingredient can be examined by sodium dodecyl sulfate polyacrylamide gel electrophoresis (SDS-PAGE) which is well known by those skilled in this art (See, for example, Laemnili Nature 227:680, 1970). In addition, the physiological bioactivity of the Guilu Erxian Gao of the present invention is evaluated by the hemopoietic effect of animals experimentation, the principle and method of which are described below.

5-fluorouracil (5-FU) can inhibit tumor cells by way of suppressing the production of pyrimidine nucleotides, and thus the 5-FU is used as an antagonist against cancers. However, 5-FU itself has a little toxicity which is sufficient to inhibit normal cells such as bone marrow, epithelial cells of gastrointestinal tract and oral mucosa. The number of white blood cells will decrease when the 5-FU is administrated to a patient, thus causing leukopenia and decreasing the therapeutic effect. Experiments were conducted via administrating 5-FU to rats, followed by Guilu Erxian Gao of the present invention. After 14 days, the rats were blooded from an eyehole vein. The blood was analyzed for the numbers of red blood cell, platelet, total white blood cell, granulocyte, monocyte and lymphocyte, respectively, to evaluate the difference of blood components in rats among various treatments.

In addition, Freund's Complete Adjuvant (FCA) is a product obtained from killed and dried Mycobacterium tuberculosis, which is similar to Bacillus Calmette-Guerin (BCG) and has the activity of immune stimulation. This experiment used FCA as control to compare the effects of FCA with those of Guilu Erxian Gao on leukopenia caused by 5-FU.

Without intending to limit it in any manner, the present invention will be further illustrated by the following examples.

EXAMPLE

Example 1

Tortoise plastron (*Cuora amboinensis*), buckhorn (*Cervus unicolor* Kerr), ginseng and medlar were used.

The tortoise plastron and buckhorn were washed with deionized water and dried in the shade at 25° C. After drying, the tortoise plastron and buckhorn were broken into pieces by a pulverizer. 200 ml of phosphoric acid (4.5%, pH 4) was added to 5.33 g of the broken tortoise plastron. On the other hand, 200 ml of phosphoric acid (4.5%, pH 4) was added to 10.66 g of the broken buckhorn. The mixtures were shaken at 45 rpm for 48 hours at 20° C., respectively, followed by filtration. The resulting filtrates were dialyzed through a dialysis membrane having molecular weight cut off 3,500 Da with deionized water for 12~16 hours to remove excess phosphoric acid and small particles.

200 ml of deionized water was added to the residues (tortoise plastron and buckhorn) obtained after filtration, respectively. The mixtures were heated in water bath at 50° C. with shaking at 45 rpm for 12 hours, followed by filtration. The resulting filtrates were dialyzed through a dialysis membrane having molecular weight cut off 3,500 Da with deionized water for 12~16 hours to remove phosphoric acid and small particles.

On the other hand, 100 ml of deionized water was added to 2 g of medlar, and another 100 ml of deionized water was added to 1 g of ginseng. The two mixtures were decocted for 24 hours, respectively, followed by filtration to obtain filtrates.

The dialyzed extracts and filtrates described above were mixed together, and concentrated at 50° C. in vacuum under reduced pressure to obtain the Guilu Erxian Gao of the present invention.

84 mg of the resulting Guilu Erxian Gao was loaded onto gel and assayed by SDS-PAGE (5% stacking gel and 12% resolving gel).

Example 2

All parameters were the same as in example 1 except that phosphoric acid used for extracting tortoise plastron and buckhorn was pH 1.2, 2.0, 5.0, 6.5 and 6.8, respectively. In the same manner, 84 mg of each resulting Guilu Erxian Gao set forth above was assayed by SDS-PAGE.

Example 3

The physiological bioactivity of Guilu Erxian Gao obtained from example 1 (i.e., extraction with phosphoric acid with pH 4) was evaluated by the hemopoietic effect in animal experimentation as described above. The collected blood samples were analyzed by Hematology Analyzer LMEK-6108K (Nihon Kohden Co.) for the numbers of red blood cell, platelet, white blood cell, granulocyte, lymphocyte, and monocyte. The result is shown in Table 1.

Control: Distilled water (20 ml/kg) was orally administrated to male rats weighted 23±2 g twice per day (10:00 AM and 4:00 PM) for 13 days.

Trial 1: Distilled water (20 ml/kg) was orally administrated to male rats weighted 23±2 g twice per day (10:00 AM and 4:00 PM) for 13 days. 5-FU was orally administrated to the rats (100 mg/kg) twice (10:00 AM and 4:00 PM) on the $8^{th}$ day.

Trial 2: Distilled water (20 ml/kg) was orally administrated to male rats weighted 23±2 g twice per day (10:00 AM and 4:00 PM) for 7 days. 5-FU was orally administrated to the rats (100 mg/kg) twice (10:00 AM and 4:00 PM) on the $8^{th}$ day. FCA (6 mg/kg) was intraperitoneally administrated once per day from $8^{th}$ to $13^{th}$ days.

Trial 3: Guilu Erxian Gao was orally administrated with a dosage of 2000 mg (20 ml/kg) to male rats weighted 23±2 g twice per day (10:00 AM and 4:00 PM) for 13 days. 5-FU was orally administered to the rats (100 mg/kg) twice (10:00 AM and 4:00 PM) on the 8th day.

TABLE 1

| Treatment | Route | Dosage | Response | | | | | |
|---|---|---|---|---|---|---|---|---|
| | | | RBC[1] ($\times 10^6/\mu l$) | Platelet ($\times 10^3/\mu l$) | WBC[2] ($\times 10^3/\mu l$) | GrC.[3] ($\times 10^3/\mu l$) | LymC.[4] ($\times 10^3/\mu l$) | MonoC.[5] ($\times 10^3/\mu l$) |
| Control | orally | 20 ml/kg × 2 × 13 | 10.66 ± 0.14 | 875.8 ± 29.1 | 7.03 ± 0.48 | 1.53 ± 0.21 | 3.85 ± 0.34 | 1.64 ± 0.11 |
| Trial 1 | orally | 20 ml/kg × 2 × 13 | 9.58 ± 0.14 | 983.5 ± 52.0 | 3.70 ± 0.23 | 0.66 ± 0.11 | 2.21 ± 0.15 | 0.84 ± 0.12 |
| Trial 2 | IP | 6 ml/kg × 1 × 6 | 9.24 ± 0.14 | 1007.0 ± 74.7 | 7.80 ± 0.69 | 2.89 ± 0.42 | 3.45 ± 0.55 | 1.47 ± 0.21 |
| Trial 3 | orally | 2000 mg/ kg × 2 × 13 | 9.95 ± 0.25 | 931.9 ± 51.6 | 5.87 ± 0.39 | 1.03 ± 0.17 | 3.35 ± 0.23 | 1.48 ± 0.18 |

[1-5]The abbreviations RBC, WBC, GrC., LymC., and MonoC. mean red blood cell, white blood cell, granulocyte, lymphocyte, and monocyte, respectively.
Data shown in Table 1 are expressed as mean ± SEM.

Figure 2:
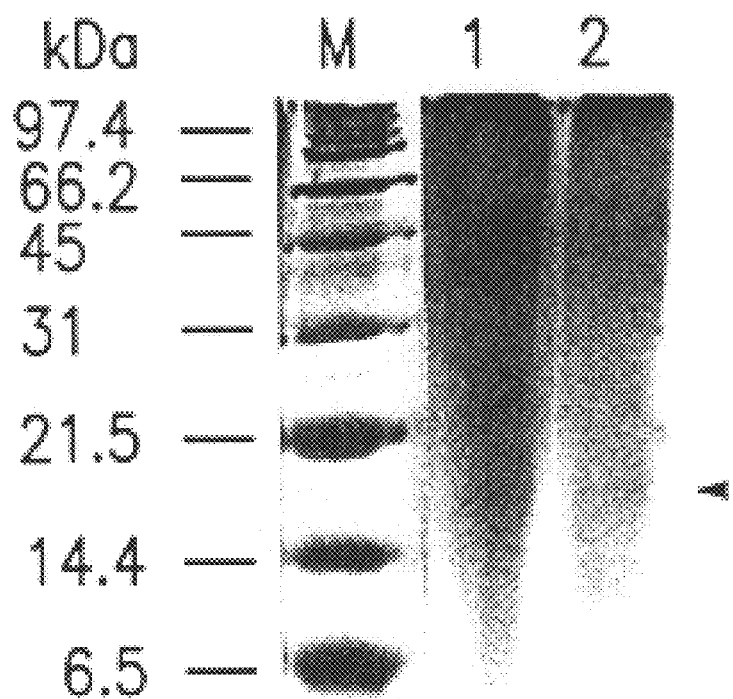
FIG. 2 is an SDS-PAGE electropherogram showing the protein bands pattern, in which lane 1 shows the Guilu Erxian Gao prepared by autoclave method; lane 2 shows that prepared by traditional method without acid treatment; and lane M is protein standard marker.
Figure 3:
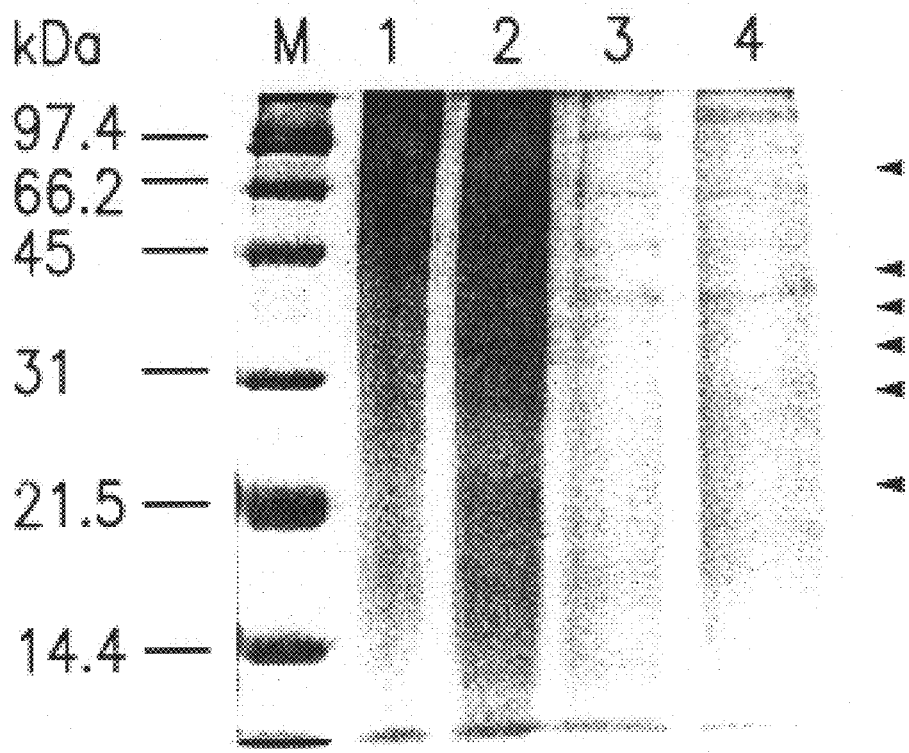
FIG. 3 is a SDS-PAGE electropherogram showing the protein bands of the Guilu Erxian Gao of the present invention treated with phosphoric acid, in which lane 1 is pH 2; lane 2 is pH 4; lane 3 is pH 6.5; lane 4 is pH 6.8; and lane M is protein standard marker.
Figure 4:
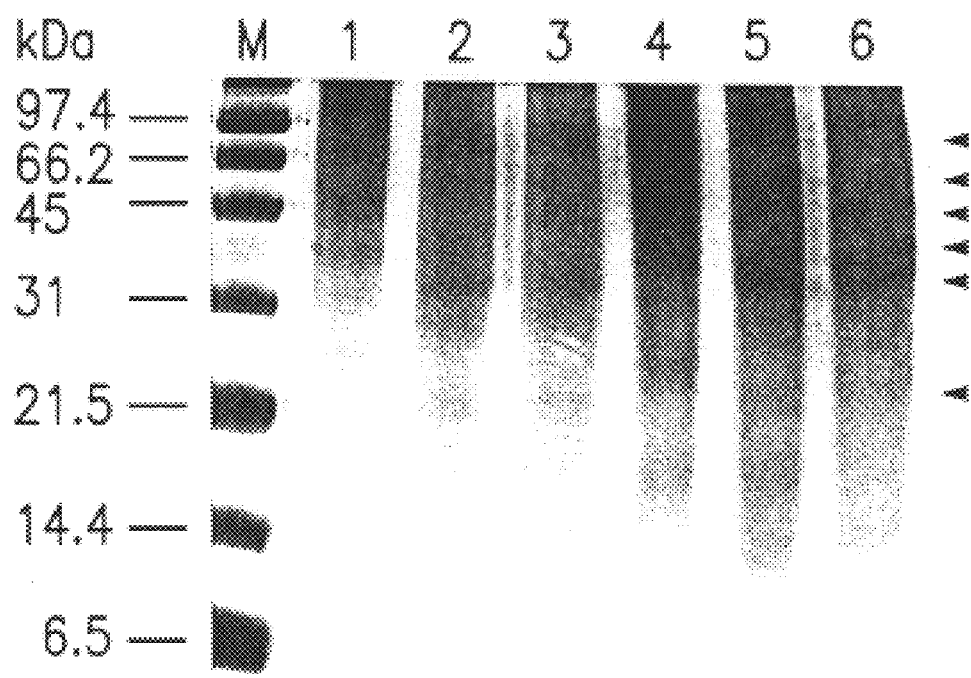
FIG. 4 is an SDS-PAGE electropherogram showing the protein bands of the Guilu Erxian Gao of the present invention treated with phosphoric acid, in which lanes 1, 4 are pH 1.2; lanes 2, 5 are pH 4; lanes 3, 6 are pH 5; and lane M is protein standard marker.

Referring to FIGS. 2–4, it is clearly shown that protein components contained in the Guilu Erxian Gao of the present invention (pH 1.2–6.8) are significantly different from those in traditional Guilu Erxian Gao obtained commercially (without acid treatment). In the groups of acid treatment (FIGS. 3–4), there are two bands at 21.5 and 31 kDa, three bands between 31 to 45 kDa, and two bands at 45 and 66 kDa appeared on the SDS-PAGE protein pattern as indicated by arrows, which is distinguishable from the pattern without acid treatment (traditional Guilu Erxian Gao).

The effect of Guilu Erxian Gao of the present invention on hemopoietic mechanism is evaluated by the various blood cells including white blood cell, granulocyte, lymphocyte and monocyte. Referring to Table 1, regarding white blood cells, means are significantly different between control (7.03±0.48'103/ml) and trial 1 (3.70±0.23'103/ml) according to unpaired student t test at p<0.01, indicating the white blood cells are inhibited by 5-FU. There is no difference between the control with trial 2 (7.80±0.69'103/ml) and trial 3 (5.87±0.39'103/ml indicating the white blood cells are recovered by both FCA and the Guilu Erxian Gao treated with acid. Means are significantly different when comparing trial 1 with trial 2 and trial 3 at p<0.01, indicating both FCA and the Guilu Erxian Gao treated with acid are effective in reversing the decrease of white blood cells resulted from 5-FU.

With regard to granulocyte, means are significantly different between control (1.53±0.21'103/ml) and trial 1 (0.66±0.11'103/ml) at p<0.01, indicating the granulocytes a inhibited by 5-FU. In addition, means are significantly different between control and trial 2 (2.89±0.42'103/ml), indicating the granulocytes are recovered and increased by FCA. No difference shows between control and trial 3 (1.03±0.17'103/ml), indicating the granulocytes are recovered by the Guilu Erxian Gao treated with acid. Means are significantly different when comparing trial 1 with trial 2 (2.89±0.42'103/ml) and trial 3 at p<0.01, indicating both FCA and the Guilu Erxian Gao treated with acid are effective in reversing the decrease of granulocyte resulted from 5-FU.

With regard to lymphocyte, means are significantly different between control (3.85±0.34'103/ml) and trial 1 (2.21±0.15'103/ml) at p<0.01, indicating the lymphocytes are inhibited by 5-FU. There is no difference between the control with trial 2 (3.45±0.55'103/ml) and trial 3 (3.35±0.23'103/ml), indicating the lymphocytes are recovered by both FCA the Guilu Erxian Gao treated with acid. Means are significantly different when comparing trial 1 with trial 2 and trial 3 at p<0.05, indicating both FCA and the Guilu Erxian Gao treated with acid are effective in reversing the decrease of lymphocyte resulted from 5-FU.

With regard to monocyte, means are significantly different between control (1.64±0.11'103/ml) and trial 1 (0.84±0.12'103/ml) at p<0.01, indicating the monocytes are inhibited by 5-FU. There is no difference between the control with trial 2 (1.47±0.21'103/ml) and trial 3 (1.48±0.18'103/ml), indicating the monocytes are recovered by both FCA the Guilu Erxian Gao treated with acid. Means are significantly different when comparing trial 1 with trial 2 and trial 3 at p<0.05, indicating both FCA and the Guilu Erxian Gao treated with acid are effective in reversing the decrease of monocyte resulted from 5-FU.

Accordingly, it is clearly demonstrated that the leukopenia caused by 5-FU can be reversed by the Guilu Erxian Gao of the present invention. In addition, the numbers of various blood cells are returned to the normal level in rats, indicating the Guilu Erxian Gao of the present invention has the ability to promote the immune system in mammals.

While the invention has been particularly shown and described with the reference to the preferred embodiment thereof, it will be understood by those skilled in the art that various changes in form and details may be made without departing from the spirit and scope of the invention.

What is claimed is:

1. A process for producing Guilu Erxian Gao, comprising the steps of:
    (a) extracting medicinal materials comprising tortoise plastron and buckhorn with an edible acid to obtain an extract;
    (b) dialyzing the extract;
    (c) decocting ginseng and medlar and filtrating to obtain a filtrate; and
    (d) concentrating the mixtures of dialyzed extract and the filtrate to form a gel solid.

2. The process as claimed in claim 1, wherein said edible acid is selected from the group consisting of acetic acid, phosphoric acid, tartaric acid, citric acid and the mixtures thereof.

3. The process as claimed in claim 2, wherein the pH of said edible acid ranges from 3.5 to 5.5.

4. The process as claimed in claim 1, wherein said edible acid is phosphoric acid.

5. The process as claimed in claim 4, wherein the pH of phosphoric acid ranges from 3.5 to 5.5.

6. The process as claimed in claim 1, wherein the tortoise plastron is selected from TESTUDINIDAE.

7. The process as claimed in claim 6, wherein the tortoise plastron is selected from *Chinemys reevesii* (Gray), *Mauremys mutica, Cuora amboinensis,* or *Cuora flavoarginata.*

8. The process as claimed in claim 1, wherein the buckhorn is selected from the ossified horn of CERVIDAE.

9. The process as claimed in claim 8, wherein the ossified horn is selected from *Cervus nippon Temminck, C. elaphus, C. albirostris Prewalski, C. unicolor Kerr, C. elaphus canadensis* or *C. macneilli Lydekker.*

10. The process as claimed in claim 1, wherein the ginseng is *Panax ginseng.*

11. The process as claimed in claim 1, wherein the medlar is the fruit of *Lycium chinensis* Mill.

12. The process as claimed in claim 1, wherein the extraction in step (a) is carried out at 25~100 rpm.

13. The process as claimed in claim 1, wherein the dialysis in step (b) is performed through a dialysis membrane.

14. The process as claimed in claim 13, wherein said dialysis membrane has a molecular weight cut off 3,500 Da.

15. The process as claimed in claim 1, wherein the concentration in step (c) is performed in vacuum under reduced pressure.

* * * * *